United States Patent [19]

Miyata

[11] 4,349,026

[45] Sep. 14, 1982

[54] REGENERATED FIBER COLLAGEN CONDOM AND METHOD OF PREPARATION

[75] Inventor: Teruo Miyata, Tokyo, Japan

[73] Assignee: Collagen Development Corp., New York, N.Y.

[21] Appl. No.: 125,538

[22] Filed: Feb. 28, 1980

[51] Int. Cl.$^3$ .............................................. A61F 5/42
[52] U.S. Cl. ............................. 128/294; 128/132 R; 128/138 R; 128/DIG. 8
[58] Field of Search ......... 128/DIG. 8, 132 R, 138 R, 128/294

[56] References Cited

U.S. PATENT DOCUMENTS

| | | | |
|---|---|---|---|
| 2,139,545 | 12/1938 | Gammeter | 428/35 |
| 3,071,477 | 1/1963 | Klevens | 128/DIG. 8 |
| 3,093,440 | 6/1963 | Bothwell | 128/294 |
| 4,233,360 | 11/1980 | Luck | 128/DIG. 8 |

*Primary Examiner*—Ellis P. Robinson
*Attorney, Agent, or Firm*—Michael Ebert

[57] ABSTRACT

A novel collagen condom consists of isotropically-strong, crosslinked, regenerated fiber collagen. A method of preparation involves the steps of at least twice dipping a mandrel into an acidic collagen dispersion; slowly removing the mandrel under spinning conditions; neutralizing and drying the membrane between dippings; crosslinking the finally dried membrane while on the mandrel and removing the membrane from the mandrel.

4 Claims, No Drawings

REGENERATED FIBER COLLAGEN CONDOM AND METHOD OF PREPARATION

This invention relates to a novel collagen condom consisting of regenerated fiber collagen which has been rendered isotropically strong by a novel method of preparation involving dipping a mandrel into an acidic dispersion of fiber collagen, e.g., tendon collagen, to produce a membrane thereof under conditions imparting isotropic strength to the membrane, neutralizing, drying and crosslinking the membrane while on the mandrel via chemical means, and removing the condom membrane from the mandrel. The neutralization is carried out preferably with an ammonia solution, e.g., $NH_4OH$, and the crosslinking by chemical means preferably with an aldehyde, e.g., glutaraldehyde, acrolein, etc.

Natural skin condoms obtained from sheep caecum are well known commercial products. They have received greater acceptance than those made of latex because of the natural feel of the skin membrane. However, the extent of production of the natural skin product depends upon the number of animals slaughtered. Thus the supply of caecum is limited, is largely imported and varies from year to year. Condoms prepared from the natural skin caecum are relatively expensive and are sold as a premium product.

A condom product made from collagen appeared on the market in Japan about ten years ago under the trademark "Koragen". The product was relatively crude, unattractive in appearance and feel and had no isotropic strength. It disappeared from the market in view of the latex product which was superior thereto. The manufacturing company failed and attempts to learn the nature of the "Koragen" process and the type of collagen employed were futile.

Large quantities of inexpensive product having properties of the sheep caecum can be produced according to this invention from regenerated fiber collagen by the process hereinbelow described. Actually, the sheep caecum product consists of collagen, albeit not of applicant's type, and the collagen fiber network structure is helpful in establishing a physically strong membrane product.

Collagen constitutes about 20 to 30 percent of the total body protein in vertebrates. It is a fibrous protein and functions primarily as a supporting tissue and scaffording for other proteins and cells. It is present throughout the body but exists in high concentrations in skin, tendon and bone.

Collagen is recovered from these tissues by a variety of techniques the oldest known method being the boiling of the tissue in water which denatures some of the collagen and forms the well-known gelatin on cooling. For use as a biomaterial however, collagen must be recovered in native, undenatured form, i.e., with little or no destruction of the basic rigid triple helical structure; (tropocollagen).

Undenatured native collagen is recovered principally by two methods, (a) solution by dissolving the collagen in acids, bases, salts or by enzyme digestion in which instances the collagen becomes actually dissolved, and (b) extraction in solid, undissolved, fiber form usually by the action of aqueous salt on minced, comminuted collagen raw material to produce a dispersion from which the solid is recovered by centrifuge, etc. Both the solution and extraction methods are well described in the collagen art.

The chemistry, molecular structure and biochemical properties of collagen have been well established. An up-to-date review article by the current inventor and others (Annual Review of Biophysics and Bioengineering, Vol. 3, p 231–253, 1974) contains an excellent compilation of references on the subject.

Native collagen is recovered in fiber form (not dissolved at all) by dispersion of the collagen in an aqueous medium and recovery by some means such as centrifuging, etc. Fiber collagen is usually recovered from animal tendon or hide as opposed to skin or bone source. Tendon, e.g., beef leg tendon, is de-sheathed, sliced and homogenized to separate individual tendon fibers in specialized "micro-cut" machines. Water is present during the machining of the tendon and the fibers become dispersed therein. The dispersion is repeatedly (2 or 3X) washed with dilute salt solution (5% NaCl) and the collagen fibers recovered by centrifuging. The fibers are washed with water to remove salt preparatory to enzyme treatment. The dispersion is treated with pancreatin, an enzyme which is very effective in dissolving elastin which encircles the fibers and binds them together. Other undesirable components, e.g., mucopolysaccharides and proteins, are also digested during this enzyme treatment which is carried out for about 24 hours at room temperature at pH of about 7–8 and enzyme concentration of 0.5 wt % based on the weight of dry collagen. After recovering the collagen fibers by centrifuge, the fibers are washed with dilute aqueous salt solution and finally with water after which they are defatted if necessary. The product is recovered from the defatting solvent, dried in air, powdered and swollen to about 1% collagen dispersions.

Hide collagen is worked up in the same manner as tendon collagen to produce fibers therefrom, but in doing so it is recommended that the hair side and flesh side be cut away and only the corium layer used.

Fiber collagen possesses high tensile strength and its high degree of natural crosslinking makes it easier to purify without degradation, particularly, during enzyme treatment wherein a milder acting enzyme may be used, and during any finishing crosslinking operation.

Collagen contains may $NH_2$ and $COOH$ groups in its structure and chemical modifications of the molecule can be readily made, e.g., all or some of the amino groups may be acylated by reaction with a mixture of acetic anhydride and acetic acid, or other anhydride such as succinic anhydride. All or some of the carboxyl groups contained in the molecule may be esterified by the standard reaction with acidified alcohol, preferably a water-soluble, aliphatic alcohol, such as methanol, ethanol, etc. In the above reactions the isoelectric point of collagen can be controlled, either negative or positive, or completely neutralized. Excellent condom products have been made from collagens which have been succinylated or methylated prior to crosslinking.

In order to obtain a strong membrane of regenerated collagen for condom production, it is essential to prepare properly the fibrous collagen dispersion for dipping. Hides and tendons are useful as starting materials, but Achilles tendon is most preferred because its collagen fibrils are aligned parallel to the tendon axis, are easily separated by mechanical agitation, and are physically strong. Collagen becomes aged with the age of the animal. During the aging process intra and intermolecular crosslinkages become introduced into the collagen fibril and the physical strength of the fibril thus increases with the age of the animal. Therefore, for purposes of this invention, tendons from older animals such as steer, cow and bull are preferred to those from calf. Tendons from pig, horse and other animals may be used in the practice of this invention, but bovine collagen is more popular and preferred.

To separate the collagen fibril bundles into individual fibrils, the tendon is chopped in a meat chopper and then processed in microcutters (e.g., those made and sold by A. Stephan U. Sohne, GmbH, West Germany) to homogenize it. Homogenized fibril is treated with a proteolytic enzyme, preferably pancreatin, at a pH in the range of 6.5 to 8.0 to ease the fibril separation. This enzyme treatment is important to make a homogeneous, well separated fibril dispersion for dipping. The enzyme destroys the elastin which binds the collagen fibrils in the bundle. Without this enzyme treatment it is extremely difficult to obtain excellent collagen dispersions.

After enzyme treatment the collagen fibril is suspended in pH 3 (lactic acid) and mechanically homogenized in a Waring blender. For adjusting the pH to 3, HCl, $H_3PO_4$, citric acid and acetic acid are also useful, but organic acids, especially lactic acid, are mostly preferable. Inorganic acids, such as HCl, swell the fibril too much and mechanical strength of the membrane prepared from these dispersions becomes weak.

Glass mandrel for dipping appears to be the best for collagen adhesion but metal and plastic mandrels may also be used. The physical strength of the condom membrane should be isotropic, that is, its longitudinal and transverse strengths must be nearly equal.

To prepare this kind of membrane, the mandrel must be taken out from the collagen acidic dispersion under a spinning clockwise action.

After drying, a second dipping is performed and the mandrel removed with the reverse counter-clockwise spinning. This dipping and removal method produces a cross-oriented fibril network in the membrane and the strength becomes isotropic. Accordingly, a number of dippings, at least twice and preferably more, make a strong and stable membrane. The spinning motion should be alternately clockwise and counter-clockwise although the order thereof is not critical.

After each dipping, neutralization of the membrane preferably by ammonia is carried out. Soon after taken from the collagen dispersion, the mandrel is dipped in $NH_4OH$ solution whereupon collagen on the mandrel is coagulated. Without neutralization, the collagen gel flows during the start of the subsequent air-drying step, and it becomes difficult to form the cross-oriented fibril network in the membrane.

After the final dipping, neutralization and drying, crosslinking is carried out preferably by soaking the membrane on the mandrel in chemical tanning solution to strengthen the mechanical property of the membrane. Chemical tanning agents, such as chromium salt and aldehyde solutions are preferred for this purpose. Chromium salt induces a green color in the membrane and produces a less swollen membrane than that produced by aldehyde treatment. Therefore, aldehyde treatment is most preferable. Even with aldehyde tanning, over-tanning results in brittleness of the membrane; while on the other hand insufficient tanning does not improve membrane strength. Therefore the optimum tanning conditions should be selected. Glutaraldehyde, formaldehyde, glyoxal, acrolein and other aldehyde are available as a tanning agent but glutaraldehyde and formaldehyde are most preferable.

The present invention is illustrated in detail in the following description. Adult bovine achilles tendon collagen is cleaned by removing fat tissue and dirt materials and chopped in a meat grinder utilizing the largest plate hole. Chopped tendon is passed through a Stephan's microcutter with a cutting aperture of 10 mm. Feeding of tendon to the machine is helped by adding ater to tendon in the machine hopper to the extent of 10 to 20 times the weight of tendon. If tendon particles larger than 2 mm remain after the first microcutter treatment, a second cutting is carried out with same cutting aperture (10 mm). A third microcutter treatment is performed with a cutting aperture of 1.0 mm. Tendon collagen is well disintegrated into fine fiber and no collagen mass remains after these microcutter treatments.

The disintegrated collagen is next treated with pancreatin (enzyme: collagen=0.5~1.5:100 on dry wt. basis) at pH 6.5~8.0 for 24 hours at 20° C. (room temperature). Pancreatin digests proteinaceous substances in the tendon collagen which bind the fibers into bundles. The removal of such substances facilitates the separation of individual collagen fibrils in the acidic dispersion. If any collagen fibril bundles remain in the acidic dispersion, membranes prepared therefrom become uneven, and membrane strength becomes weak. Most preferable conditions for pancreatin treatment are: ratio of pancreatin to collagen 1:100 on dry wt. basis; pH 7.4; temperature 20° C., and incubation period 24 hours. To adjust the pH a buffer solution of M/15 phosphate is recommended. In order to depress microorganism growth the addition of a bactericide, e.g., 0.1 wt. % of methylparaben is preferably added to enzyme solution. The ratio of enzyme solution to dry collagen is recommended to be 20:1 (solution:collagen). Other proteolytic enzymes having optimum pH in the neutral region such as trypsin, papain, ficin may be used in place of pancreatin.

Pancreatin treated tendon is centrifuged to collect the collagen after which it is washed with water, and centrifuged. Washed collagen is added to water (collagen:water=0.5~1.5:100 on dry wt. basis), and homogenized well in a Waring blender to disperse the fibrils. Lactic acid is added to the dispersion to adjust the pH to 2.5-4.0 (preferably about 3.0) and the dispersion is blended again in a Waring blender. Addition of 0.1 wt. % methylparaben to the acidic dispersion as a preservative is again recommended. Blending of the acidic collagen dispersion separates the collagen fibrils and makes a viscous gel consisting of homogeneously dispersed collagen fibrils. Blending produces heat because of the high viscosity of the acidic dispersion; therefore the temperature of the dispersion should be kept under 30° C. by cooling the container in an ice bath. Temperatures over 40° C. induce collagen denaturation and should be avoided. If the collagen concentration in the acid dispersion is higher than 1.5 wt. %, formation of a uniform film on the mandrel in the subsequent dipping steps becomes difficult, because of the high viscosity of the dispersion; while concentrations lower than 0.5 wt. % require extra dippings to form a membrane having sufficient thickness. Collagen concentration of 1.0 wt. % (collagen:water=1:99) is best and strong membranes are obtained by three dippings at this concentration.

Acidic gel dispersion is deairated under vacuum before it is used for dipping. A glass mandrel is inserted into the acidic collagen dispersion and lifted slowly with clockwise spinning of mandrel to orient collagen fibril at about 45° to the longitudinal axis of mandrel. The ratio of removing rate to spinning rate of mandrel should be carefully controlled.

The mandrel with a collagen film thereon is soaked in 1–10% NH$_4$OH solution for 1 to 3 min. to neutralize (coagulate) the collagen film. Preferred soaking conditions are 1 minute in 5% NH$_4$OH solution.

Coagulated collagen film on the mandrel is dried in a warm air stream (lower than 80° C.); preferably at 50 to 60° C. Air temperature higher than 80° C. sometimes induces denaturation of the collagen. The neutralized, dried membrane is now ready for a second dipping.

In the second dipping the spinning of mandrel is counter-clockwise, otherwise the procedure steps are the same as those of the first dipping including neutralization and drying. A third dipping, if necessary, is carried out at exactly the same procedure (clockwise spinning of mandrel) as that of first dipping including neutralization and drying. Alternatively, the first spinning could be performed in a counterclockwise direction and the second in a clockwise direction. The direction of spinning should alternate with each successive dipping.

After the last dipping dried collagen membrane on the mandrel is tanned by soaking in a tanning solution. Glutaraldehyde and formaldehyde are preferable as the tanning agent. The degree of tanning depends on agent concentration, pH of solution, temperature and soaking time. The following conditions are recommended:

glutaraldehyde: 0.35%, pH 8.5 (0.02 MNa$_2$HPO$_4$), 20° C., 1 minute.
formaldehyde: 1.0%, pH 8.5 (0.02 MNa$_2$HPO$_4$ buffer), 20° C., 2 minutes.

Tanned membrane on the mandrel is washed with water for 10 seconds and air-dried in a warm air flow of 50° C.

In order to remove the membrane from the mandrel it must be swollen with an appropriate solution. When the membrane becomes wet it expands and the contact force between the membrane and mandrel is lessened. Twenty percent (20%) propylene glycol is a good agent for this purpose and also acts as a lubricant for the collagen condom. After soaking in 20% propylene glycol for 1 minute, the membrane is rolled out from the mandrel. A rubber band may be glued to a upper end of the membrane on the mandrel before swelling. The band becomes part of the condom, is rolled in the condom after removal from the mandrel, and is helpful in the proper use of the condom.

Tensile and tear strengths of the collagen condom thus prepared are greater than those of the commercially available natural sheepskin product. The properties are indicated in the following table in comparison with that of the natural products.

TABLE I

Tensile and tear strength of collagen condoms prepared in Examples 1 and 2 versus commercial condom from sheep caecum. Values are averaged:

|  | Exam. 1 | Exam. 2 | Natural |
|---|---|---|---|
| thickness (mil) | 13 | 13 | 33 |
| tensile (lb/in$^2$) | 5200 | 4500 | 1300 |
| tear (lb/in) | 400 | 350 | 160 |

As indicated above collagen condoms prepared by the method disclosed in this application are stronger than the natural sheepskin product and the uniformity of membrane is superior to that of the natural product. The feel of the membrane is as good or better than that of the natural product because of the thinness of the membrane.

The present invention may be further understood from the following example.

EXAMPLE 1

One kilogram adult bovine achilles tendon was cleaned by removing fat tissue and other debris. Tendon was chopped with a meat grinder having a cutting plate with a ¼-inch hole. Chopped tendon and 20 liters of water were passed through a Stephan's microcutter, (MVD-12 A) with cutting ring aperture of 10 mm. The cutting was repeated. Two cuttings were then performed with a cutting ring aperture of 1.0 mm. The suspension of fine fiber after microcutting was centrifuged to separate water. Recovered collagen was resuspended in 10 l. of M/15 phosphate buffer, pH 7.4, containing 3 g of pancreatin, and 0.1% methylparaben and allowed to stand for 24 hours at room temperature (20° C.).

After enzyme treatment the fiber was collected by centrifuge, resuspended in 20 l of water for washing and collected again by centrifuge. Collagen content of the collected fiber was 30%.

One hundred grams (100 g.) of centrifuged fiber (30 grams collagen in dry basis) was suspended in 3.0 l of water containing 0.1% methylparaben (collagen concentration 1.0 wt. %) and homogenized well in a Waring blender. Lactic acid was added dropwise to the collagen suspension to pH 3.0 under gentle homogenization. The suspension became viscous and changed to a pasty liquid. The suspension was blended in a Waring blender for 5 minutes, during which the temperature of suspension was kept lower than 30° C. by cooling with ice water.

Acidic collagen fibril suspension was then subjected to deairation under vacuum. To accelerate the deairation, agitation was applied to the dispersion.

A clean glass mandrel was dipped into the deairated acidic suspension and lifted slowly with gentle clockwise spinning to orient the fibril at about 45° against the longitudinal axis of the mandrel. Soon after removal the mandrel was soaked in 5% NH$_4$OH for 1 minute and placed in a stream of warm air of 50° C. The mandrel was spun during drying. After drying, a second dipping was carried out with counter-clockwise spinning of the mandrel and the collagen film was air-dried after ammonia soaking in the same way as the first dipping. A third dipping was conducted with clockwise spinning of the mandrel, with neutralization and drying as carried out in prior dippings.

The finally dried collagen membrane on the mandrel was tanned in 0.35% glutaraldehyde (0.02 M Na$_2$HPO$_4$ pH 8.4) for 1 minute, washed with tap water for 10 seconds and air-dried with warm air.

The membrane was removed from the mandrel after soaking in 20% propylene glycol for 10 seconds and stored in the same solution. The thickness of collagen condom thus produced is very uniform and thinner (average 13 mil) than the commercial natural sheepskin product (average 33 mil). Its feel (by finger touch) is excellent. Average strength in tensile and tear was superior to that of the natural product as indicated in Table 1 above.

EXAMPLE 2

Dry collagen membrane on the mandrel after three dippings was produced by the method exactly similar to that of Example 1.

The membrane was tanned in 1% formaldehyde solution (0.02 M $Na_2HPO_4$ pH 8.4) for 2 minutes at room temperature (20° C.), washed with tap water for 10 seconds and air-dried in a stream of warm air at 50° C. A rubber band was glued to the end of the dry membrane, the membrane rewetted with 20% propylene glycol and rolled out from the mandrel. The membrane displayed properties corresponding to the properties of the product of Example 1 above.

The mandrel employed in the process described is preferably tapered to facilitate removal of the finished membrane therefrom. A typical mandrel is roughly 30 cm. in length over which the diameter tapers from 6 cm. down to 5 cm. The mandrel is dipped vertically into the collagen dispersion and lifted slowly under spinning. The rates of lifting and spinning are controlled so that fibril orientation of about 45° is obtained. Fibril orientation on the mandrel is visibly observable and a little practice is required; however, after neutralization the orientation becomes quite clear. The duration of the dipping is roughly 10 to 20 sec. when employing the glass mandrel to which the collagen gel exhibits greater adherence. Mandrels made of other materials vary in gel adherence but generally the above mentioned times suffice. Caution should be observed in that too rapid dipping and removal induces air bubble formation in the membrane. The mandrel is removed at a rate of about 1 to 5 cm./sec. With regard to the rate of rotation of the spinning mandrel, the speed should not be such that the force of the spin strips the adhered collahen from the mandrel. Actually, the rate is relatively slow, about 1 full rotation per 10 to 15 cm. of mandrel removal.

Irradiation may be employed for the crosslinking but it is not recommended. Radiation equipment is expensive if not otherwise available, and irradiation treatment is less desirable than chemical tanning. Ultraviolet radiation is carried out as follows: After drying following the final dipping and neutralization, the membrane on the mandrel is subjected to a 30 watt UV lamp at a distance of about 10 cm. for a period of 10 to 60 min., preferably 30 min. The mandrel should be rotated during the exposure. After treatment the membrane is removed as in Example 1. Irradiation with gamma rays requires about 5 to 24 hours treatment for sufficient crosslinking and is not most practicable.

Having described the invention in a manner that it may be practiced by those skilled in the art:

What is claimed is:

1. As an article of manufacture a condom consisting of an isotropically-strong membrane of crosslinked regenerated, fiber collagen.

2. An article of claim 1 in which the collagen is animal tendon collagen.

3. An article of claim 1 in which the collagen membrane is crosslinked by treatment with an aldehyde.

4. An article of claim 1 in which the collagen is selected from the group consisting of esterified and acylated collagens.

* * * * *